United States Patent [19]

Waldvogel

[11] Patent Number: 5,070,859
[45] Date of Patent: Dec. 10, 1991

[54] LARYNGOSCOPE

[75] Inventor: Herman H. Waldvogel, Paudex, Switzerland

[73] Assignee: Narco-Med AG., Kreuzlingen, Switzerland

[21] Appl. No.: 415,640

[22] Filed: Oct. 2, 1989

[30] Foreign Application Priority Data

Sep. 5, 1989 [CH] Switzerland .................. 03220/89-9

[51] Int. Cl.$^5$ ........................... A61B 1/00; A61B 1/26
[52] U.S. Cl. ..................................... 128/10; 128/777; 73/862.54
[58] Field of Search .................. 128/10, 11, 777, 9, 128/6, 20, 15, 16, 774; 73/865.7, 862.38, 862.51, 862.54

[56] References Cited

U.S. PATENT DOCUMENTS

| | | | |
|---|---|---|---|
| 3,785,381 | 1/1974 | Lower et al. | 73/862.54 |
| 3,888,117 | 6/1975 | Lewis | 128/20 |
| 4,263,900 | 4/1981 | Nicholson | 128/20 |
| 4,295,465 | 10/1981 | Racz et al. | 128/11 |
| 4,384,570 | 5/1983 | Roberts | 128/4 |
| 4,426,884 | 1/1984 | Palchaninoff | 128/774 |
| 4,488,873 | 12/1984 | Bloomfield et al. | 128/777 |
| 4,556,052 | 12/1985 | Müller | 128/11 |
| 4,791,940 | 12/1988 | Hirschfeld | 128/777 |
| 4,841,987 | 6/1989 | Brown et al. | 128/777 |
| 4,884,223 | 11/1989 | Ingle et al. | 73/862.15 |

Primary Examiner—Edward M. Coven
Assistant Examiner—Mark J. Graham
Attorney, Agent, or Firm—Brady, O'Boyle & Gates

[57] ABSTRACT

A laryngoscope (1) is equipped with a dynamometer in order to be able to measure and record the force expended per unit time by an anesthetist during the vacating and keeping unobstructed of a path in the oral and pharyngeal cavity for the introduction of a tube into the trachea. The dynamometer comprises pressure elements arranged in the spatula contact surface (17) and, respectively, in the proximity of the spatula joint. By means of this measurement, an objective judgement can be made with regard to the anesthetist's skill; on the other hand, the pharmaceuticals utilized for the intubation procedure can be objectively documented by measured values with regard to their pharmacological properties, such as, for example, the production of rapid and intense muscle relaxation.

5 Claims, 3 Drawing Sheets

LARYNGOSCOPE

The invention relates to a laryngoscope.

BACKGROUND OF THE INVENTION

Laryngoscopes are utilized, in particular, in human patients for depressing the retrolingual region during introduction of a tube past the glottis into the trachea (windpipe). Local anesthesia or narcosis, with or without a muscle relaxant, is required for intubation in order to obtain hyporeflexia and muscle relaxation of the pharyngeal and laryngeal musculature.

Thus far, it has been impossible to make an objective analysis of the intubation procedure: descriptive criteria (e.g. difficult intubation—easy intubation) are needed for the anesthetic record as well as in clinical research, for novel muscle relaxants, for example. For this reason, it is extremely difficult for the pharmaceutical industry to test pharmaceuticals for local anesthetics, muscle relaxants, and anesthetics with respect to their pharmacological properties and clinical usability to ascertain their usefulness, on account of different anatomical characteristics of the individual patients, the varying skills of the anesthetists, and the aforementioned, subjective criteria.

SUMMARY OF THE INVENTION

The invention is based on the object of providing objective criteria and features of optimum intubation, on the one hand, in order to perfect the training of future anesthetists and, on the other hand in order to be able to determine objectively the effect of local anesthetics, muscle relaxants, and anesthetics.

The above object has been attained by the invention as characterized in the claims, with the aid of a laryngoscope making it possible to measure the force expended for vacating a path, and maintaining this path unobstructed, for a tube to be introduced into the trachea.

BRIEF DESCRIPTION OF THE DRAWINGS

Examples of the laryngoscope of the invention will be described in greater detail below with reference to the drawings wherein.

DESCRIPTION OF THE PREFERRED EMBODIMENTS

Figure 1:
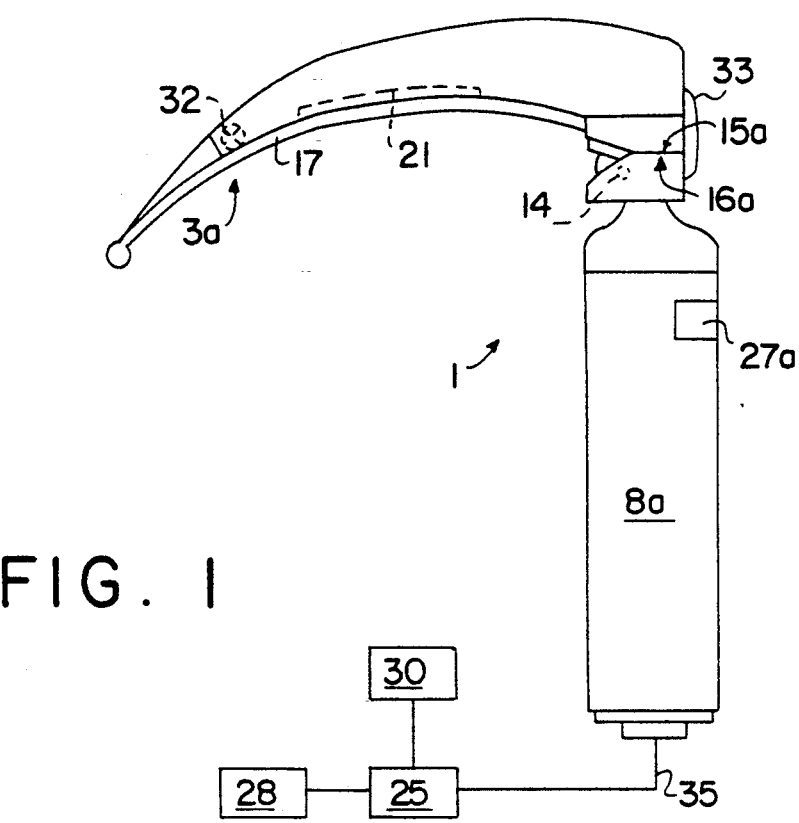
FIG. 1 is a lateral view of a laryngoscope according to this invention.
Figure 2:
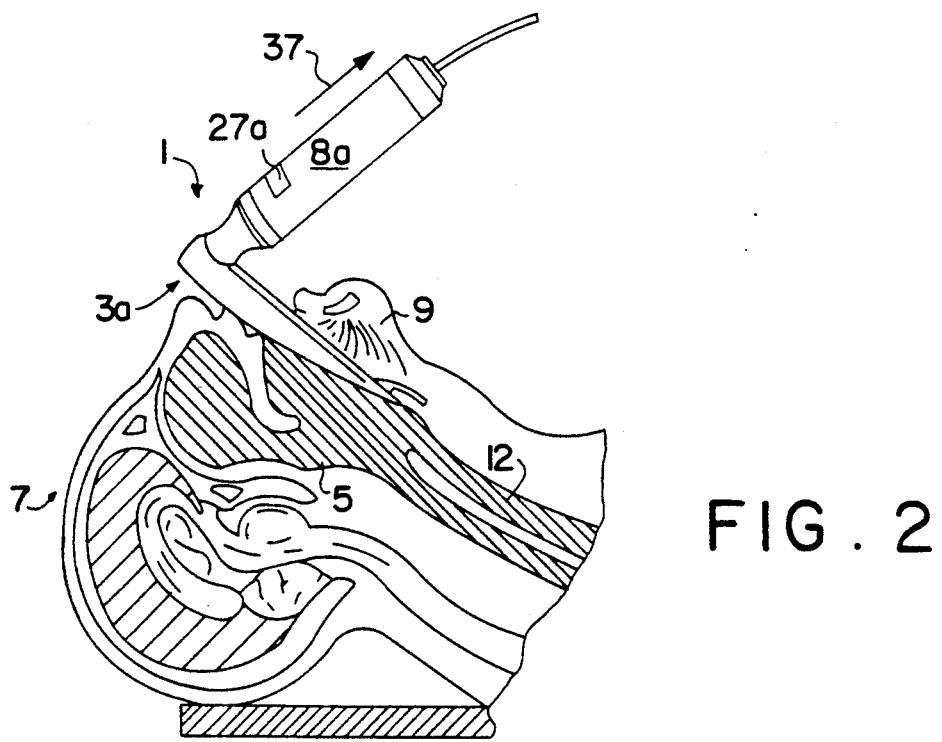
FIG. 2 shows one use of the laryngoscope.

The unfolded spatula 3a of the laryngoscope 1 illustrated in FIG. 1 is introduced into the oral and pharyngeal cavity 5 of a patient 7 shown in FIG. 2. By pulling at the handle 8a of the laryngoscope 1, the anesthetist depresses the retrolingual region 9 in order to vacate the path for a tube (not shown) past the glottises into the trachea 12 and to keep such path unobstructed during introduction of the tube.

The spatula 3a is attached by way of a joint 14 to the handle 8a and is unfolded in FIG. 1 approximately at a right angle to this handle; with its deflection stop surface 15a, the spatula rests on the deflection stop surface 16a of the handle 8a on the side facing away from the spatula tip.

Figure 3:
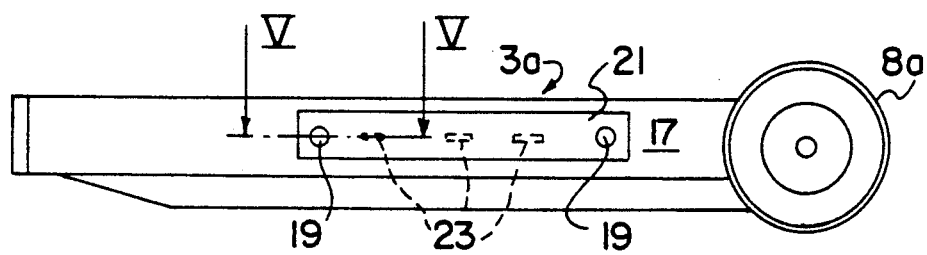
FIG. 3 is a top view of the contact surface of the spatula of the laryngoscope.
Figure 4:
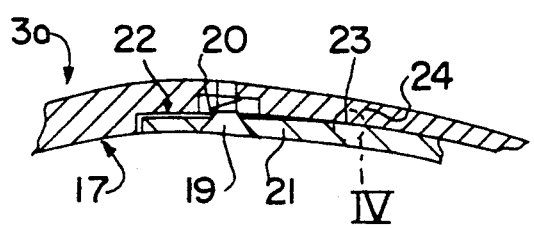
FIG. 4 shows a sectional view along line V—V in FIG. 3.
Figure 5:
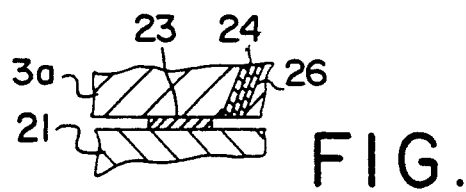
FIG. 5 shows an enlarged view of a pressure measuring element attached in the spatula, in correspondence with portion IV in FIG. 4.

A contact plate 21 is located approximately in the center of the contact surface 17 of the spatula 3a, illustrated in FIG. 3; this contact plate is guided by two guide means 19 each provided with a cap in a depression 22 of the contact surface 17, the caps preventing a dropping out from the contact surface. The contact plate 21 is slightly urged against the caps of the guide means 19 by two springs 20; FIG. 4 shows only one guide means 19 and one spring 20. In the depression 22, three piezoelectric pressure measuring elements 23 are glued in place as measuring elements of a dynamometer. The electric leads 24 to the pressure measuring elements 23 are cast into a duct 26, shown in FIG. 5 and leading to the topside of the spatula 3a. By means of the two springs 20, the contact plate 21 is kept at a distance from the surface of the pressure measuring elements 23 in order to avoid interfering information.

The dynamometer consists of the aforementioned pressure measuring elements 23, an evaluating unit 25, an indicator 27a in the handle 8a, another movable indicator 28, and a writer 30 as the recording device for the time-dependent recording of the measured values from the pressure measuring elements 23, evaluated by the evaluating device 25. The current supply for the dynamometer and for a light 32 in the forward third of the spatula 3a for illuminating the oral and pharyngeal cavities 5 during intubation is not illustrated.

The light 32 and the pressure measuring elements 23 are connected via a flexible cable 33, illustrated schematically in FIG. 1, with a cable (not shown) extending within the handle 8a, this latter cable being extended at the lower end of the handle by means of a further cable 35 to the evaluating device 25

For performing an intubation, the spatula 3a is inserted as described above in the oral and pharyngeal cavity 5 and pulled by the anesthetist, using the handle 8a, against the retrolingual region 9 in the direction of arrow 37 in FIG. 2; during this step, the contact plate 21, pressing onto the base 9 of the tongue, is urged against the pressure elements 23. The data measured by each of the three pressure elements 23 are averaged by the evaluating device 25, multiplied by a value (lever arm) considering the distance from the joint 14, and the result, calculated in each instance at constant time intervals, is indicated by the indicator 27a. The result is furthermore recorded by the writer 30 in dependence on the time.

These recorded results permit conclusions regarding the "mechanical" skills and thus the training status of the anesthetist. Several occurrences of force applications which deviate from normal values and are too vigorous and/or last too long a time admit the conclusion that the anesthetist shows inadequate routine skills.

If, in addition to the time-force curve, the blood pressure of patient 7 is recorded, then a strongly rising blood pressure during the period of highest expenditure of force yields the conclusion that the intensity of anesthesia is not adequate When testing the effect of various anesthetics, the course of the time-force curve can be utilized as an objective means of comparison.

Figure 6:
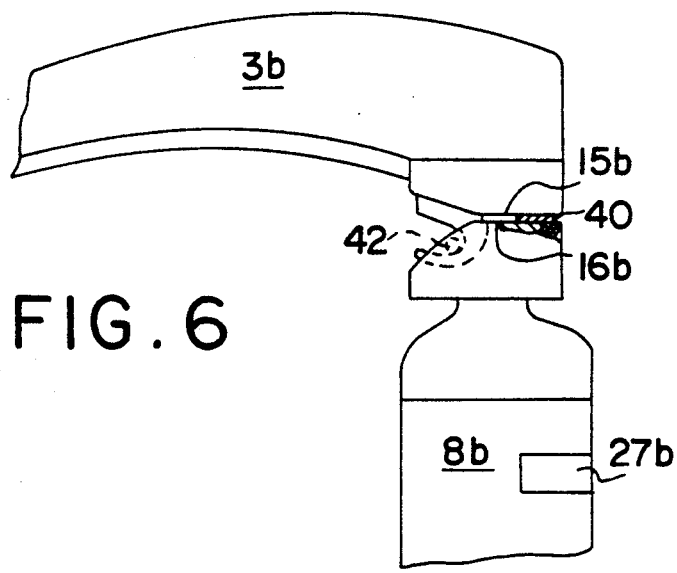
FIG. 6 shows a modification of the laryngoscope.
Figure 7:
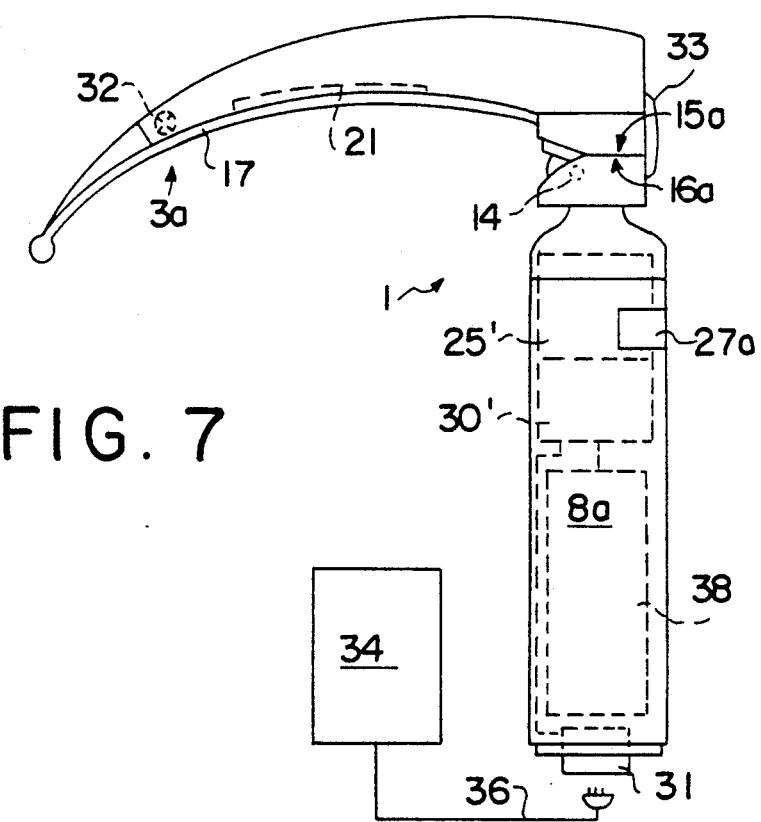
FIG. 7 shows a schematic modification for use on the forms of the invention of FIGS. 1 and 6.

Instead of arranging the pressure elements 23 in the contact surface 17 preferably approximately in the center of the spatula 3a underneath the pressure plate 21, it is also possible, as shown in FIG. 6, to provide a single pressure measuring element 40 on a deflection stop surface 16b of a handle 8b fashioned analogously to the handle 8a. The deflection stop surface 15b of a spatula 3b designed analogously to the spatula 3a then presses during the intubation procedure on the pressure measuring element 40. The data measured by the pressure measuring element 40 are converted, in the evaluating device 25, with a value characteristic for the spatula 3b based on its length and on the position of the pressure measuring element 40, into a force, indicated on an indicator 27b of the handle 8b analogous to the indicator 27a, and recorded by the writer 30. The advantageous feature of this arrangement as compared with the first-described laryngoscope resides in the elimination of the flexible cable 33 as a line for the measured values of the pressure elements 23; this cable could under certain circumstances lead to difficulties upon repeated sterilization of the spatula 3a. The lead to the lamp 32 is here realized by electrical contacts (not shown) between the deflection stop surfaces 15b and 16b. The spatula 3b, as contrasted to the spatula 3a, can be hung into and removed from a joint 42 at the upper end of the handle 8b. Thereby, the spatula 3b can be subjected to an extremely effective sterilization after each performed intubation while the separate handle 8b with the installed electronic unit is sterilized more gently.

In both forms of the invention, instead of evaluating the data of the force expended per unit time by way of the separate evaluating unit 25 and recording with the use of the writer 30, the data can also be processed by means of an evaluating device 25 installed in the handle 8a, 8b; this latter evaluating device indicates, on the one hand, the respectively determined value as described above by means of the indicator 27a, 27b in the handle 8a, 8b and stores, on the other hand, the time-dependent data, in a memory 30 installed in the handle 8a, 8b. This memory can be connected via an interface 31 in the handle 8a, 8b to an external read-out device 34 by way of a connectable connecting line 36. A battery 38 is mounted in the handle 8a or 8b to provide current supply to the electronic components (memory, evaluating device, indicator 27a or 27b).

The data stored in the memory can also be retrieved via the interface directly by a computer (not shown) and then processed in order to determine, for example, averaged values, "individual diagrams" of the various anesthetists, statistical scattering, etc.

Screens can likewise be used as the recording devices, besides analog- and digital-operating writers 30.

The laryngoscope of this invention makes it possible for the first time to measure objectively the force expended per unit time for vacating the path, and keeping it unobstructed, for a tube to be introduced into the trachea. By means of this measurement, the anesthetist's skill can be judged, on the one hand, while, on the other hand, the pharmaceuticals utilized for the intubation procedure can be objectively documented by measured values with respect to their pharmacological properties, such as, for example, production of rapid and intense muscle relaxation.

I claim:

1. A laryngoscope for endotracheal intubation comprising, an elongated blade shaped to fit into the oral pharynx of a patient and having a concave formed inner side for depressing the retrolingual region, a handle connected to said blade, a dynamometer having a force measuring element, said force measuring element connected on said concave formed inner side for measuring the force expended for vacating and keeping unobstructed a path for a tube to be introduced into the trachea, and said dynamometer having recording or storing means connected with said force measuring element for recording or storing the measured force in dependence of the time for determining the skill of the anesthetist and the effect of the applied anesthetic.

2. A laryngoscope according to claim 1, wherein said concave formed inner side of said blade includes a cavity, said force measuring element being a piezoelectrical force measuring element connected at the bottom of said cavity, and a movable contact plate fitted in said cavity in said concave formed inner side of said blade and covering said piezoelectrical force measuring element for transmitting thereto the force expended by said blade for vacating and keeping unobstructed the path for a tube to be introduced into the trachea.

3. A laryngoscope according to claim 1 or 2, wherein said laryngoscope includes a battery, said battery and said recording or storing means being displaced in said handle, a display connected to said dynamometer for displaying the instantaneous measured force, an external device, and an interface having connecting means for connecting said interface to said external device to transfer the data recorded or stored by said recording storing means thereto after an endotracheal intubation.

4. A laryngoscope for endotracheal intubation comprising, an elongated blade shaped to fit into the oral pharynx of a patient, a handle, pivot means pivotally connecting said blade at one end of said handle, a deflection stop between said blade and said handle limiting the pivoting of said blade away from said handle, a dynamometer having a force measuring element, said force measuring element connected on said deflection stop to have pressure applied thereto when said blade is pivoted away from said handle towards the limit of said deflection stop upon introduction of said blade into the oral pharynx of the patient, said force measuring element for measuring the force expended for vacating and keeping unobstructed a path for a tube to be introduced into the trachea, and said dynamometer including recording or storing means connected with said force measuring element for recording or storing the measured force in dependence of the time for determining the skill of the anesthetist and the effect of the applied anesthetic.

5. A laryngoscope according to claim 4, wherein said laryngoscope includes a battery, said battery and said recording or storing means being displaced in said handle, a display connected with said dynamometer for displaying the instantaneous measured force, an external device, and an interface having connecting means for connecting said interface to said external device to transfer the data recorded or stored by said recording or storing means thereto after an endotracheal intubation.

* * * * *